United States Patent
Kim et al.

(10) Patent No.: US 9,623,156 B2
(45) Date of Patent: Apr. 18, 2017

(54) METHOD OF PREPARING COATING FILM CONTAINING NITROGEN MONOXIDE ON SURFACE OF MATERIAL USING CATECHOLAMINE

(71) Applicant: POSTECH ACADEMY-INDUSTRY FOUNDATION, Pohang-si, Gyeongsangbuk-do (KR)

(72) Inventors: Won Jong Kim, Pohang-si (KR); Jihoon Kim, Pohang-si (KR); Haeshin Lee, Daejeon (KR); Seonki Hong, Daejeon (KR)

(73) Assignee: POSTECH ACADEMY-INDUSTRY FOUNDATION, Pohang-si, Gyeonsangbuk-Do (KR)

(*) Notice: Subject to any disclaimer, the term of this patent is extended or adjusted under 35 U.S.C. 154(b) by 450 days.

(21) Appl. No.: 13/860,899

(22) Filed: Apr. 11, 2013

(65) Prior Publication Data

US 2014/0127277 A1    May 8, 2014

(30) Foreign Application Priority Data

Nov. 5, 2012 (KR) .................. 10-2012-0124499

(51) Int. Cl.
| | | |
|---|---|---|
| *A61L 31/10* | (2006.01) | |
| *A61L 27/54* | (2006.01) | |
| *A61L 29/16* | (2006.01) | |
| *A61L 27/34* | (2006.01) | |
| *A61L 29/08* | (2006.01) | |
| *A61L 31/16* | (2006.01) | |

(52) U.S. Cl.
CPC .............. *A61L 31/10* (2013.01); *A61L 27/34* (2013.01); *A61L 27/54* (2013.01); *A61L 29/085* (2013.01); *A61L 29/16* (2013.01); *A61L 31/16* (2013.01); *A61L 2300/114* (2013.01)

(58) Field of Classification Search
None
See application file for complete search history.

(56) References Cited

U.S. PATENT DOCUMENTS

| | | | | |
|---|---|---|---|---|
| 5,405,919 A | * | 4/1995 | Keefer et al. | 525/377 |
| 2005/0288260 A1 | | 12/2005 | Hrabie et al. | |
| 2008/0149566 A1 | * | 6/2008 | Messersmith | C08J 7/123 |
| | | | | 210/702 |
| 2008/0175881 A1 | * | 7/2008 | Ippoliti | A61L 31/10 |
| | | | | 424/423 |
| 2012/0237605 A1 | | 9/2012 | Messersmith et al. | |

FOREIGN PATENT DOCUMENTS

| | | | |
|---|---|---|---|
| WO | WO 01/92215 | * | 12/2001 |
| WO | WO0192215 A2 | | 12/2001 |
| WO | 2007085254 A1 | | 8/2007 |
| WO | WO2010096320 A2 | | 8/2010 |

OTHER PUBLICATIONS

Hrabie et al. (Chem. Rev., 102, 1135-1154, 2002) Chemistry of the Nitric Oxide-Releasing Diazeniumdiolate . . . .*
Jihoon Kim; Mussel-Inspired Surface Chemistry as a New Platform for Nitric-Oxide Delivery; 2012 Spring Academic Conference; The Polymer Society of Korea.
Korean Notice of Allowance.
International Search Report to corresponding International Application No. PCT/KR2013/002825 dated Jun. 14, 2013.

* cited by examiner

*Primary Examiner* — Tigabu Kassa
(74) *Attorney, Agent, or Firm* — Lucas & Mercanti, LLP

(57) ABSTRACT

A method of coating surfaces of various body-implantable materials with control-releasable nitrogen monoxide using a catecholamine, more particularly, technology of preparing a coating film containing a diazeniumdiolate functional group on a surface of a material to be coated using a catecholamine, is provided. The coating film prepared by the method has advantages in that nitrogen monoxide can be stably supplied under an in vivo environment, and can be suitably used in a living body without causing cytotoxicity. Therefore, among the materials having a coating film formed on a surface thereof, the body-implantable material is especially expected to be widely used for medical and health applications including treatment of ischemic disorders such as arteriosclerosis through controlled release of nitrogen monoxide, regulation of penile erections, antibacterial and antiviral effects, and wound healing.

11 Claims, 14 Drawing Sheets

METHOD OF PREPARING COATING FILM CONTAINING NITROGEN MONOXIDE ON SURFACE OF MATERIAL USING CATECHOLAMINE

CROSS-REFERENCE TO RELATED APPLICATION

This application claims priority to and the benefit of Korean Patent Application No. 2012-0124499, filed Nov. 5, 2012, the disclosure of which is incorporated herein by reference in its entirety.

BACKGROUND

1. Field of the Invention

The present invention relates to a method of coating surfaces of various materials with control-releasable nitrogen monoxide using a catecholamine, and, more particularly, to technology of preparing a coating film containing a diazeniumdiolate functional group on a surface of a material using a catecholamine.

2. Discussion of Related Art

Nitrogen monoxide (NO) is a bio-regulatory material exhibiting potent medical effects in various fields, which was selected as the "molecule of the year" by the US journal Science in 1992, and was a main topic for the Nobel Prizes in physiology and medicine in 1998. Nitrogen monoxide serves as a signal transduction material or a product formed by an immune response in a human body, and has various effects such as vasodilatation, neurotransmission, regulation of hair cycle, formation of reactive nitrogen-containing intermediates, regulation of penile erections, antibacterial effects, antiviral effects and wound healing. Especially, nitrogen monoxide has a very short in vivo half-life of less than 6 seconds, and exhibits its various effects when it is present in a gaseous state. Therefore, nitrogen monoxide has an advantage in that its effects are exhibited only in a local site in which it is released in vivo, and thus is highly applicable as a body-implantable material.

There are various kinds of compounds in which nitrogen monoxide can be released from a surface of the body-implantable material. For example, such compounds include an organic nitrate or ester, an iron-nitrosyl complex, sydnonimine, a C-nitroso compound, S-nitrosothiol (R—S—NO), a 1-substituted diazen-1-ium-1,2-diolate, etc. However, conventional techniques for physically adsorbing the various compounds onto a surface of an implantable medical device have problems in that nitrogen monoxide may be released in sites rather than a desired local site since its coatability is unstable under in vivo conditions, and may not be released at a sufficient amount. Also, a xerogel, to which a diazeniumdiolate formed by a conventional sol-gel synthesis method using an aminosilane is attached, has problems in that it is very expensive and difficult to synthesize the aminosilane, and its coating thickness is high. Also, a conventional method of attaching a nitrogen monoxide transmitter containing a sulfur group to a surface of a metal using a self-assembled monolayer has an advantage in that it is applicable only to certain metals.

Therefore, there has been an increasing interest in methods by which a large amount of nitrogen monoxide can be attached to any materials with high stability to effectively release the nitrogen monoxide. Accordingly, the formed coating film for releasing nitrogen monoxide has characteristics in that its thickness should not be so large as to cause inconvenience in applying body-implantable materials, and is simplified and inexpensive to be industrially applicable. Also, the coating film should not exhibit toxicity at a cellular level, and its concentration and release time should be easily controlled.

However, there has been no report on a method of preparing a nitrogen monooxide-releasing coating film satisfying the above-described requirements so far.

SUMMARY OF THE INVENTION

Therefore, to solve the prior-art problems, the present inventors have made many attempts to develop a method of stably preparing a coating film containing nitrogen monoxide on a surface of a material. Accordingly, the present invention is completed based on these facts.

Accordingly, the present invention is designed to solve the problems of the prior art, and it is an object of the present invention to provide a method capable of enabling delayed release and/or controlled release of nitrogen monoxide from surfaces of various materials using a biomimetic catecholamine containing a diazeniumdiolate functional group.

However, the prior-art problems to be solved according to the present invention are not limited to the above-described problems, and other problems which are not disclosed herein may be made apparent to those skilled in the art by the detailed description provided below.

One aspect of the present invention provides a method of preparing a nitrogen-monoxide-containing coating film on a surface of a material. Here, the method includes synthesizing a diazeniumdiolate functional group using a catecholamine.

According to one exemplary embodiment of the present invention, the synthesizing a diazeniumdiolate functional group using a catecholamine may include:

(a) immersing a material whose surface is to be coated in a basic solution at pH 8.5 to pH 11, (b) adding a catecholamine to the basic solution used in operation (a) and keeping the material in the resulting mixture, (c) drying the material after the keeping of the material in operation (b), (d) introducing the material dried in operation (c) into a reactor containing the basic solution, (e) purging the reactor used in operation (d) with argon (Ar) gas, and (f) introducing nitrogen monoxide into the reactor used in operation (e) to synthesize a diazeniumdiolate functional group.

According to another exemplary embodiment of the present invention, the basic solution used in operation (a) may be at least one solutions elected from the group consisting of a physiological saline solution, water, and tetrahydrofuran (THF).

According to still another exemplary embodiment of the present invention, the keeping of the material in operation (b) may be performed for 6 to 72 hours.

According to another exemplary embodiment of the present invention, the catecholamine added in operation (b) may be in the form of powder or an aqueous solution obtained by dissolving the powder.

According to another exemplary embodiment of the present invention, the drying of the material in operation (c) may be performed using argon (Ar), helium (He), or nitrogen ($N_2$) gas.

According to another exemplary embodiment of the present invention, the basic solution used in operation (d) may be at least one solution selected from the group consisting of sodium methoxide (NaOMe), methanol (MeOH), tetrahydrofuran (THF), and sodium hydroxide (NaOH).

According to another exemplary embodiment of the present invention, the basic solution used in operation (d) may be present at a concentration of 0.1 to 0.5 M.

According to another exemplary embodiment of the present invention, the purging of the reactor in operation (e) is performed one to three times at a pressure of 10 to 30 psi.

According to another exemplary embodiment of the present invention, the introducing of the nitrogen monoxide in operation (f) may be performed at a pressure of 80 to 150 psi.

According to another exemplary embodiment of the present invention, the method may further include sonicating the material in methanol after operation (f).

According to another exemplary embodiment of the present invention, the catecholamine may be selected from the group consisting of dopamine, dopamine quinone, alpha-methyldopamine, norepinephrine, dihydroxyphenylalanine (DOPA), alpha-methyldopa, droxidopa, and 5-hydroxydopamine.

According to another exemplary embodiment of the present invention, the coating film may have a thickness of 40 to 60 nm.

According to yet another exemplary embodiment of the present invention, the material may be a body-implantable material selected from the group consisting of a stent, a catheter, a subcutaneous implant, a chemical sensor, a lead, a pacemaker, a vascular graft, a wound dressing, a penile implant, an implantable pulse generator (IPG), an implantable cardiac defibrillator, and a nerve stimulator.

BRIEF DESCRIPTION OF THE DRAWINGS

The above and other objects, features and advantages of the present invention will become more apparent to those of ordinary skill in the art by describing in detail exemplary embodiments thereof with reference to the attached drawings, in which.

DETAILED DESCRIPTION OF EXEMPLARY EMBODIMENTS

Figure 1:
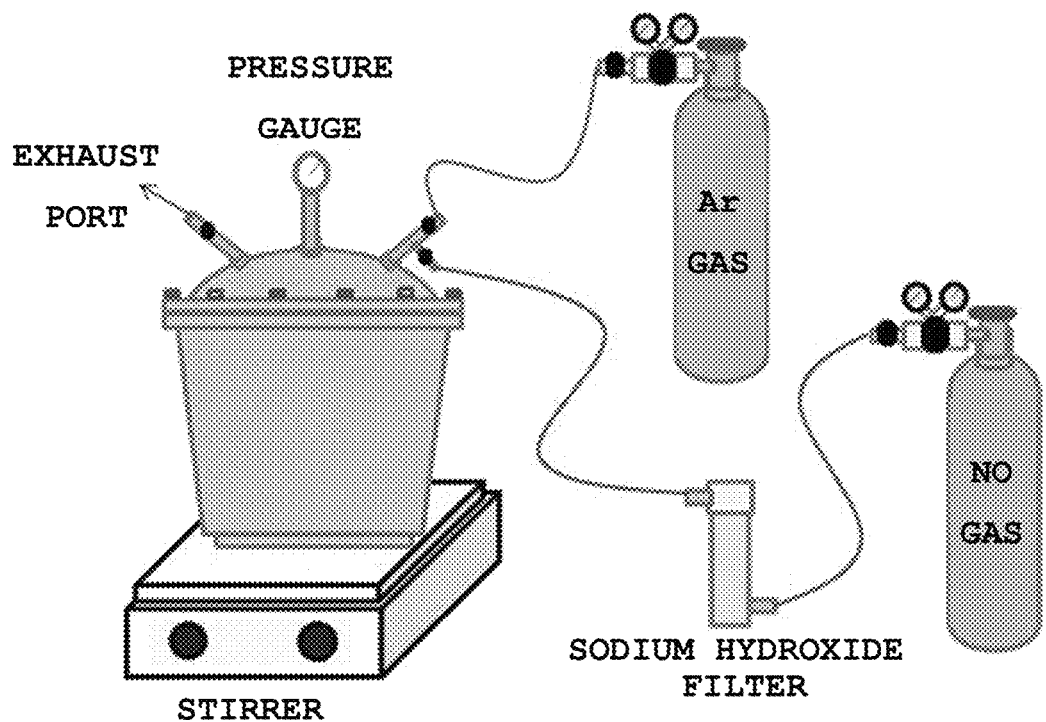
FIG. 1 is a schematic diagram showing a reactor (device) for preparing a coating film containing nitrogen monoxide on a surface of a body-implantable material according to the present invention.

Hereinafter, exemplary embodiments of the present invention will be described in detail. However, the present invention is not limited to the embodiments disclosed below, but can be implemented in various forms. The following embodiments are described in order to enable those of ordinary skill in the art to embody and practice the present invention.

Although the terms first, second, etc. may be used to describe various elements, these elements are not limited by these terms. These terms are only used to distinguish one element from another. For example, a first element could be termed a second element, and, similarly, a second element could be termed a first element, without departing from the scope of exemplary embodiments. The term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

The terminology used herein is for the purpose of describing particular embodiments only and is not intended to be limiting of exemplary embodiments. The singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements, components and/or groups thereof, but do not preclude the presence or addition of one or more other features, integers, steps, operations, elements, components and/or groups thereof.

With reference to the appended drawings, exemplary embodiments of the present invention will be described in detail below. To aid in understanding the present invention, like numbers refer to like elements throughout the description of the figures, and the description of the same elements will not be reiterated.

The present invention provides a method of preparing a nitrogen-monoxide-containing coating film on a surface of a material. Here, the method is characterized in that it includes synthesizing a diazeniumdiolate functional group using a catecholamine.

The term "catecholamine" refers to a single molecule containing a hydroxyl group (—OH) as an ortho group and various alkylamines as para groups in the benzene ring. As a benzene ring containing the hydroxyl group as the ortho group, or derivatives of materials having various structures at the alkylamines of the para groups, the catecholamine includes dopamine, dopamine-quinone, alpha-methyldopamine, norepinephrine, dihydroxyphenylalanine (DOPA), alpha-methyldopa, droxidopa, or 5-hydroxydopamine.

Materials in which a bio-synthetic polymer such as an ethyleneimine polymer, an ethylene glycol polymer, a propylene glycol polymer, a lactic acid polymer, or an ϵ-caprolactone polymer, and a copolymer thereof such as an ethylene glycol/propylene glycol copolymer, an ethyleneimine/ethylene glycol copolymer, a lactic acid/glycolic acid copolymer, a lactic acid/ethylene glycol copolymer, a lactic acid-glycolic acid-ethylene glycol copolymer, a lactic acid-glycolic acid-ethylene glycol-ethylene glycol copolymer, a caprolactone/ethylene glycol copolymer, or a polypeptide-based block copolymer are attached to the alkylamine groups of the catecholamine may be used as main chains to which a diazeniumdiolate may be attached.

In the present invention, the "diazeniumdiolate" is used as a functional group which is chemically bound to the main chain of the nitrogen-monoxide-transferred coating film to store and release nitrogen monoxide, and the diazeniumdiolate may be represented by the Equation: RR'N—N(O)═NOR". A diazeniumdiolate compound may be stably stored in a solid phase, have high solubility in water, and control release types such as release rate and mode according to a structure of a residue to which the diazeniumdiolate functional group is bound. Also, the diazeniumdiolate compound may be decomposed at a bio temperature and a pH condition, has various release types according to a pH value, and releases 2 molecules of nitrogen monoxide per diazeniumdiolate functional group. Therefore, when the diazeniumdiolate compound is included in a transmitter, the nitrogen monoxide may be formed at a relatively high concentration. As a result, the coating film according to the present invention has a diazeniumdiolate functional group, which is able to release nitrogen monoxide, as a side chain when the coating film is exposed to a functional group for storing and releasing nitrogen monoxide under in vivo conditions.

In the present invention, the term "transmitter" refers to a material capable of transferring nitrogen monoxide, and, more particularly, to a coating film for enabling controlled release of nitrogen monoxide, which contains a diazeniumdiolate functional group according to the present invention.

The diazeniumdiolate functional group may be obtained by allowing nitrogen monoxide to react with a secondary amine, as shown in the following Formula 1.

Formula 1

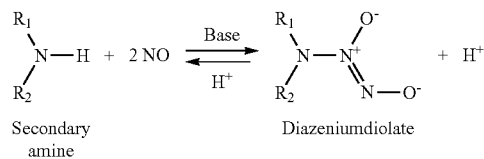

Secondary amine      Diazeniumdiolate

To prepare a polymer containing the diazeniumdiolate functional group, an oligomer having a secondary amine nitrogen in the chain backbone (that is, the residue $R_1$—N—$R_2$ in Formula 1 bound in a chain in a main longitudinal direction thereof), or having a secondary amine nitrogen in a side chain thereof may be used.

According to one exemplary embodiment of the present invention, a secondary amine nitrogen is formed on a surface of a material to be coated through self-polymerization of the catecholamine as shown in Formula 1, and nitrogen monoxide is allowed to react with the secondary amine nitrogen to prepare a nitrogen-monoxide-containing coating film. This scheme is as represented by the following Formula 2.

Formula 2

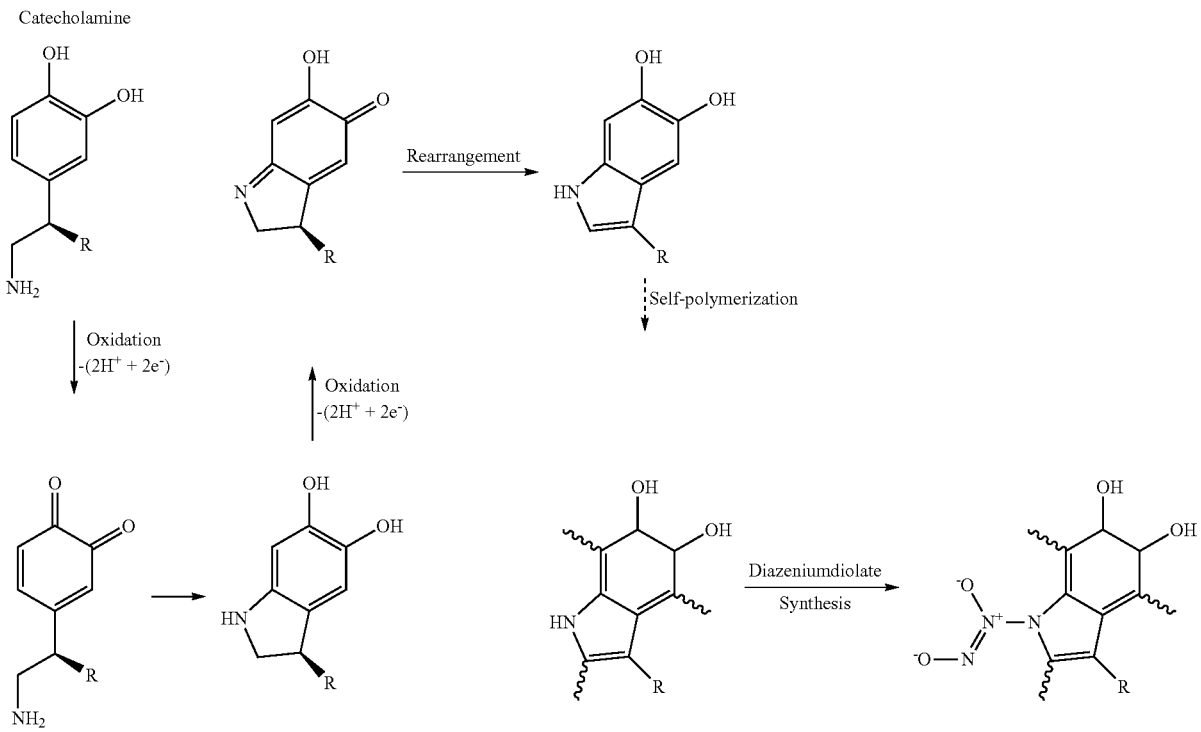

The diazeniumdiolate functional group may control release characteristics of nitrogen monoxide under the control of functional groups corresponding to $R_1$ and $R_2$ in Formula 1 or a functional group corresponding to R in Formula 2. In particular, when a structure has atoms, such as F, O, and N, which are able to form a hydrogen bond, storage and release characteristics of nitrogen monoxide may be controlled.

As provided in the present invention, the coating film enabling controlled release of nitrogen monoxide is a polymer having a main chain and functional groups for storing and releasing nitrogen monoxide. Here, the functional groups are bound to the main chain by means of a chemical bond. The chemical bond generally means a covalent bond. For example, when a non-covalent bond such as biotin-avidin interaction has an intermolecular force comparable with the covalent bond, the non-covalent bond is included in a category of the chemical bond connecting the main chain with the functional group for storing and releasing nitrogen monoxide.

As a biomimetic catecholamine that may be used for the main chain of the coating film prepared in the present invention, catecholamines such as dopamine, dopamine-quinone, alpha-methyldopamine, norepinephrine, dihydroxyphenylalanine (DOPA), alpha-methyldopa, droxidopa, or 5-hydroxydopamine may be used. As listed in one exemplary embodiment of the present invention, dopamine and norepinephrine represented by Formula 3 may be preferably used. As a commercially available material, the dopamine forms a salt with hydrogen chloride, and has a molecular weight of 189.64, and the norepinephrine has a molecular weight of 169.18.

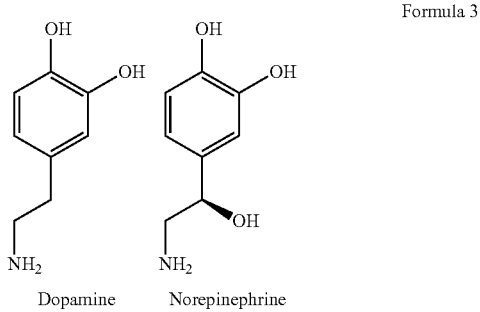

Formula 3

Dopamine    Norepinephrine

In the present invention, the term "biomimetic catecholamine" is derived from the fact that dihydroxyphenylalanine (DOPA) known to be included at a large amount in *Mytilus edulis* foot protein-5 (Mefp-5) that is an absorbent protein of a blue mussel, and dopamine mimicking a structure of lysine are polymerized on surfaces of various materials under basic conditions to form a coating film having a nano-sized thickness, and thus has the same meaning as a catecholamine.

Also, the synthesis of the diazeniumdiolate functional group using the catecholamine is characterized in that it includes:

(a) immersing a material whose surface is to be coated in a basic solution at pH 8.5 to pH 11;

(b) adding a catecholamine to the basic solution used in operation (a) and keeping the material in the resulting mixture;

(c) drying the material after the keeping of the material in operation (b);

(d) introducing the material dried in operation (c) into a reactor containing the basic solution;

(e) purging the reactor used in operation (d) with argon (Ar) gas; and/or (f) introducing nitrogen monoxide into the reactor used in operation (e) to synthesize a diazeniumdiolate functional group.

That is, according to one exemplary embodiment of the present invention, to synthesize a diazeniumdiolate functional group to prepare a coating film containing nitrogen monoxide on a desired surface of a material, a body-implantable material or a medical appliance is put into a basic solution at pH 8.5 to 11, a catecholamine is sprayed in the form of powder or an aqueous solution (a neutral/acidic aqueous solution) obtained by dissolving the powder, and kept for 8-24 hours to form a catecholamine coating film. Thereafter, the body-implantable material or medical appliance on which the catecholamine coating film is formed is put into a basic solution, and nitrogen monoxide gas is added under a strong pressure to store nitrogen monoxide on a surface of the body-implantable material or medical appliance. As a result, it was confirmed that the controlled release of nitrogen monoxide under in vivo conditions is enabled. In this case, the controlled release of nitrogen monoxide is enabled by controlling an alkyl group in the catecholamine used.

The synthesis of the diazeniumdiolate functional group using the catecholamine will be described in further detail, as follows. Operation (a) is an operation of preparing a solvent for self-polymerization of a catecholamine. In this operation, a physiological saline solution, water, or tetrahydrofuran (THF) may be used as the basic solution alone or in combination. Phosphate buffered saline (PBS) used according to one exemplary embodiment of the present invention may be preferably used, but the present invention is not limited thereto.

Operation (b) is an operation of inducing self-polymerization of the catecholamine. In this operation, the keeping of the material may be performed for 6 to 72 hours, preferably 12 to 36, and most preferably 24 hours, but the present invention is not limited thereto. For example, the material may be kept for a sufficient time to induce the self-polymerization, depending on a condition of the material. In this case, the catecholamine may be added in the form of powder, or a neutral or acidic aqueous solution obtained by dissolving the powder.

The material whose self-polymerization is induced in operation (b) may be dried in operation (c). Here, the drying of the material may be performed using pure air, argon (Ar), helium (He), or nitrogen ($N_2$) gas. However, kinds of gases having no effects on films formed before operation (c) may be used without limitation. To perform the synthesis of the diazeniumdiolate functional group, the dried material is then introduced into a reactor containing a basic solution. In this case, the basic solution used in operation (d) may be a solution including one or two or more of sodium methoxide (NaOMe), methanol (MeOH), tetrahydrofuran (THF), and sodium hydroxide (NaOH), any of which is present at a concentration of 0.1 to 0.5 M in the solution. According to one exemplary embodiment of the present invention, a mixed solution including sodium methoxide (NaOMe) and methanol (MeOH) at a concentration of 0.5 M may be most preferably used as the basic solution, but the present invention is not limited thereto.

Also, the purging of the reactor with the argon gas in operation (e) may be performed one to three times at a pressure of 10 to 30 psi. According to one exemplary embodiment of the present invention, the purging of the reactor with the argon gas may be most preferably performed twice at a pressure of 20 psi, but the present invention is not limited thereto.

Next, to synthesize a diazeniumdiolate functional group capable of releasing nitrogen monoxide, operation (f) of introducing nitrogen monoxide into the purged reactor is performed. In this case, the nitrogen monoxide may be introduced at a pressure of 40 psi to 200 psi, and preferably a pressure of 80 psi to 150 psi. According to one exemplary embodiment of the present invention, the nitrogen monoxide may be most preferably introduced at a pressure of 80 psi, but the present invention is not limited thereto.

In addition, after introduction of the nitrogen monoxide, a reaction may be performed for 1 to 5 days to prepare a catecholamine polymer coating film containing a diazeniumdiolate functional group on a surface of the material. After preparation of the coating film, the sonicating of the material in methanol may be further performed to remove impurities.

It is revealed that the coating film prepared according to the present invention has a nano-sized thickness, is biosynthesized at a higher level than a bio-synthetic polymer, PLGA, approved by the FDA, and exhibits high stability in an acid, a base, or an organic solvent. That is, the coating film prepared according to the present invention may have a thickness of 40 to 60 nm, but the present invention is not limited thereto.

Based on these results, the present invention may provide a coating technique for enabling controlled release of nitrogen monoxide by stably forming a coating film when nitrogen dioxide is applied to a surface of a material to be coated, especially, a surface of an artificial device positioned in a human body.

In the present invention, the term "material" is applicable as long as its surface can be coated to enable controlled release of nitrogen monoxide. Preferably, the material may be a substance used to coat a surface of a body-implantable material.

As such, the term "body-implantable material" refers to all kinds of materials that are rooted at a position at which physiological effects can be exhibited through release of nitrogen monoxide in a body of an animal including a human or a mammal, and have a surface provided with a transmitter for enabling controlled release of nitrogen monoxide. Such an implantable material may be partially inserted into the body, but the entire part of the implantable material may not be necessarily inserted into the body. For example, a connection unit such as a pipe or a wire may extend out from the body. Also, the term "body-implantable medical appliance" or "(body) medical appliance" is included in the "body-implantable material," and includes all kinds of equipment for treatment, surgery, surgical operation, diagnosis, or examination of a human or a mammal. The medical appliance may be partially or totally inserted into the body. For example, only a probe or sensor part of the entire medical appliance may be inserted into the body for a predetermined period of time. Therefore, the body-implantable material may be a stent, a catheter, a subcutaneous implant, a chemical sensor, a lead, a pacemaker, a vascular graft, a wound dressing, a penile implant, an implantable pulse generator, an implantable cardiac defibrillator, or a nerve stimulator, but the present invention is not limited thereto.

The coating film containing nitrogen monoxide according to the present invention is used to form a thin film having a nano-sized thickness, and contains a primary amine (—$NH_2$), a hydroxyl group (—OH), or a catechol group (a benzene ring containing a hydroxyl group as an ortho group), which may further react with the main chain structure. Therefore, the coating film may further include a material exhibiting a pharmacological effect in an inner part or a surface thereof. That is, according to the present invention, the body-implantable material may be used to improve the innate effects of the implantable material or the medical appliance by enabling controlled release of nitrogen monoxide, but may be used to enable additional release of a material having a pharmacological effect in addition to the nitrogen monoxide. The nitrogen monoxide is known to facilitate wound healing and control neurotransmission, as well as to relax vascular smooth muscles. In particular, the nitrogen monoxide has disinfectant and antiviral effects as well. Also, the nitrogen monoxide exhibits the most excellent antiviral effect against human papilloma virus (hPV), and also shows an excellent disinfectant activity against *Staphylococcus aureus* (*S. aureus*), *Staphylococcus epidermidis* (*S. epidermidis*), and *Pseudomonas aeruginosa* (*P. aeruginosa*) among bacteria. Also, other materials having a pharmacological effect may be immobilized in the form of a conjugate bound to the coating film by means of a chemical bond, and may be simply dispersed without forming a chemical bond in a thin film. Examples of the materials having a pharmacological effect are not limited. For example, when a material includes a material for preventing thrombus formation or blood coagulation, an antioxidant, an antiphlogistic agent, a wound healing promoter, or an antibacterial agent, the material may exhibit a synergic effect with a body-implantable material for releasing nitrogen monoxide. In this case, examples of the corresponding material having a pharmacological effect include a vascular endothelial growth factor (VEGF), an antibacterial agent, an antiviral agent, an antiphlogistic agent, vitamin C, acetylsalicylic acid, an antihyperlipidemic agent, a thrombolytic agent, an antithrombotic agent, and heparin, but the present invention is not limited thereto.

In the present invention, the term "controlled release" refers to an operation of releasing nitrogen monoxide, or an active compound, which can instantly form the nitrogen monoxide under in vivo conditions, from a surface of a material including a body-implantable material at a predetermined rate. Therefore, the controlled release encompasses a meaning that the nitrogen monoxide or the active compound is not intermittently released from a surface of the material in an unpredictable manner. The release rate of nitrogen monoxide is maintained in a steady state (referred to as timed release or zero-order release), that is, a state in which a certain amount of nitrogen monoxide is regularly released for a given period of time (referred to as a state in which nitrogen monoxide may or may not be explosively released at the beginning), or a state in which nitrogen monoxide may be released in a rate-gradient manner (referred to as rate-gradient release). The rate-gradient release encompasses a meaning that a concentration of the nitrogen monoxide or the active compound released from a surface of the material changes with time. For example, when the nitrogen monoxide or active compound capable of instantly forming the nitrogen monoxide is directly exposed to an in vivo environment, the life span of the nitrogen monoxide or the active compound is reduced. Therefore, slowing down the release of these molecules from the coating film for transferring the prepared nitrogen monoxide at a given rate or explosively releasing the molecules according to a release design corresponds to controlled release.

Hereinafter, the present invention will be described in further detail with reference to the following preferred Examples so as to facilitate better understanding of the present invention. However, it should be understood that the following Examples are given by way of illustration of the present invention only, and are not intended to limit the scope of the present invention.

Preparative Example 1

Preparation of Catecholamine Polymer Coating Film Containing Diazeniumdiolate Functional Group To prepare a coating film containing a diazeniumdiolate functional group capable of releasing nitrogen monoxide using a catecholamine, first, a silicon wafer for analysis or an austenitic stainless steel 316L (10 mm×10 mm, thickness: 3 mm) was put into a 12-well plate in which each well contained 1 mL of phosphate buffered saline (PBS) at pH 8.5. Next, 2 mg of each of dopamine, which is a catecholamine containing an alkyl group including a primary amine, and norepinephrine, which is a catecholamine containing an alkyl group including a primary amine and a hydroxyl group, was put in the form of powder into each well. Subsequently, a catecholamine polymer coating film was formed on a surface of the silicon wafer or the stainless steel by keeping the resulting mixture at room temperature for 24 hours so as to facilitate self-polymerization of the dopamine or norepinephrine. After the keeping of the resulting mixture, the resulting sample was thoroughly washed with water, and dried with argon (Ar). To synthesize a diazeniumdiolate functional group on a secondary amine formed on a surface of the prepared catecholamine polymer coating film, the following procedure was performed. The sample having a catecholamine polymer coating film formed thereon was put into each of 70 mL vials containing 3 mL of 0.5 M sodium methoxide (NaOMe)/methanol, and the reaction vials were put into a reactor. Then, the reactor was purged twice with argon gas at a pressure of 20 psi. Thereafter, nitrogen monoxide was introduced into the reactor at a pressure of 80 psi, and reacted for 3 days to synthesize a diazeniumdiolate functional group. A schematic diagram of the reactor used in the reaction is shown in FIG. 1. Subsequently, the sample having a catecholamine polymer coating film formed thereon to include a diazeniumdiolate functional group was sonicated in methanol for 5 minutes to remove impurities such as sodium methoxide or unadsorbed nitrogen monoxide gas. Then, the sample was stored at −20° C. before use.

Figure 2:
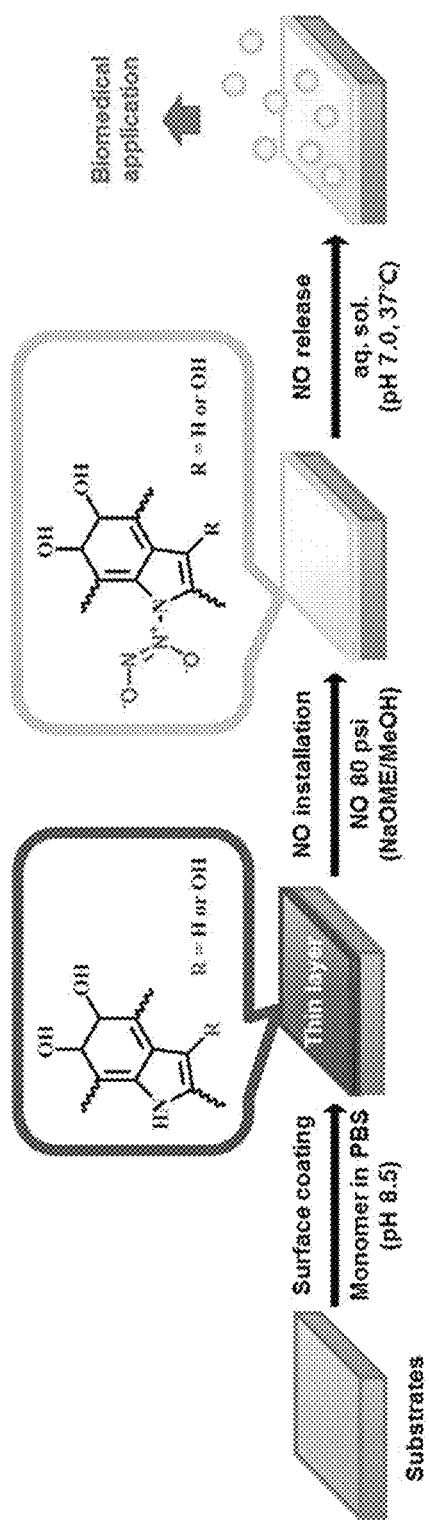
FIG. 2 is a schematic diagram showing a method of preparing a coating film containing nitrogen monoxide on a surface of a body-implantable material according to the present invention.

The following Formula 4 is a scheme illustrating preparation of a dopamine coating film having a diazeniumdiolate functional group attached thereto, and the following Formula 5 is a scheme illustrating preparation of a norepinephrine polymer coating film having a diazeniumdiolate functional group attached thereto. A primary amine of the catecholamine was subjected to oxidation and self-polymerization to form a secondary amine. Then, the formed secondary amine was subjected to diazeniumdiolation to store nitrogen monoxide. In this Preparative Example, entire operations of a method of preparing a nitrogen-monoxide-containing coating film are as shown in FIG. 2.

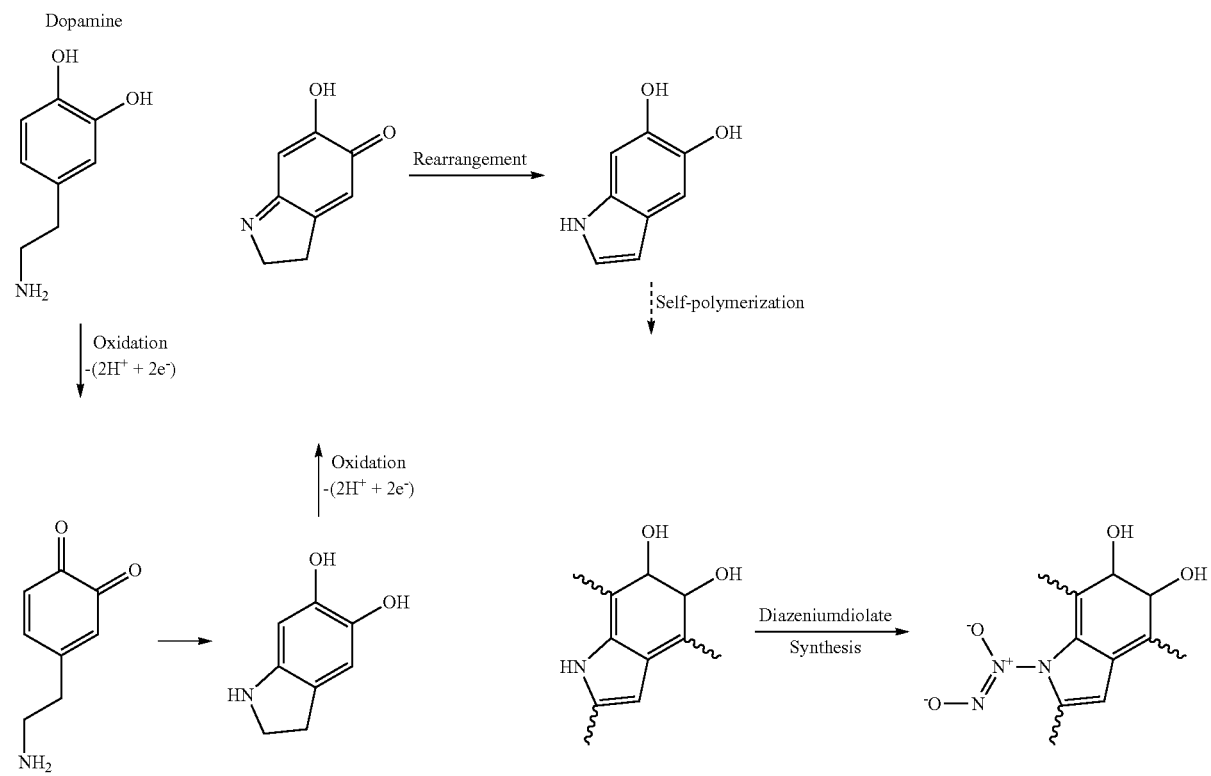

Formula 4

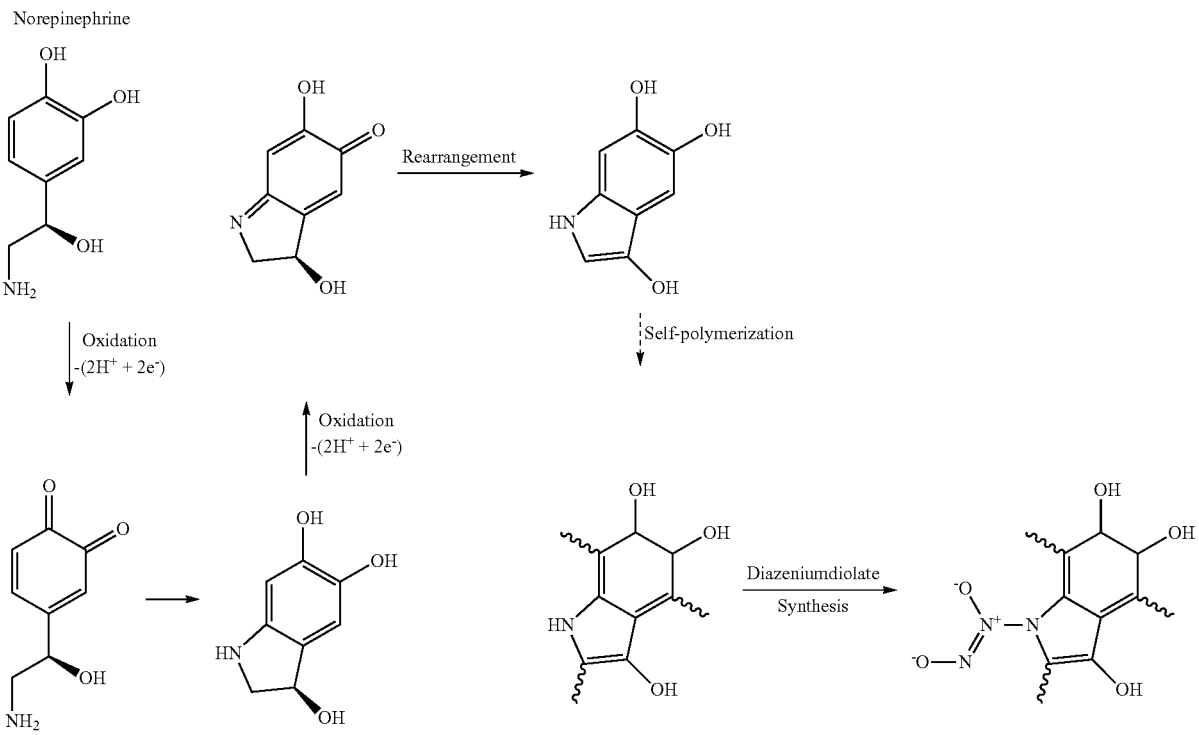

Example 1

Analysis of Characteristics of Catecholamine Polymer Coating Film Containing Prepared Diazeniumdiolate Functional Group To determine the characteristics of the catecholamine polymer coating film containing a diazeniumdiolate functional group prepared in Preparative Example 1 an experiment was performed as follows.

<1-1> Analysis of Characteristics of Catecholamine Polymer Coating Film Containing Diazeniumdiolate Functional Group Using Atomic Force Microscope (AFM)

Each of a dopamine polymer coating film (pDA), a dopamine polymer coating film (pDA-NO) containing a diazeniumdiolate functional group, and a norepinephrine polymer coating film (pNOR-NO) containing a diazeniumdiolate functional group was formed on a silicon wafer for analysis using the same method as described in Preparative Example 1. Then, a surface of each coating film was observed using an atomic force microscope (Dimension 3100 equipped with Nanoscope V controller, Veeco Instruments Inc., USA).

Figure 3:
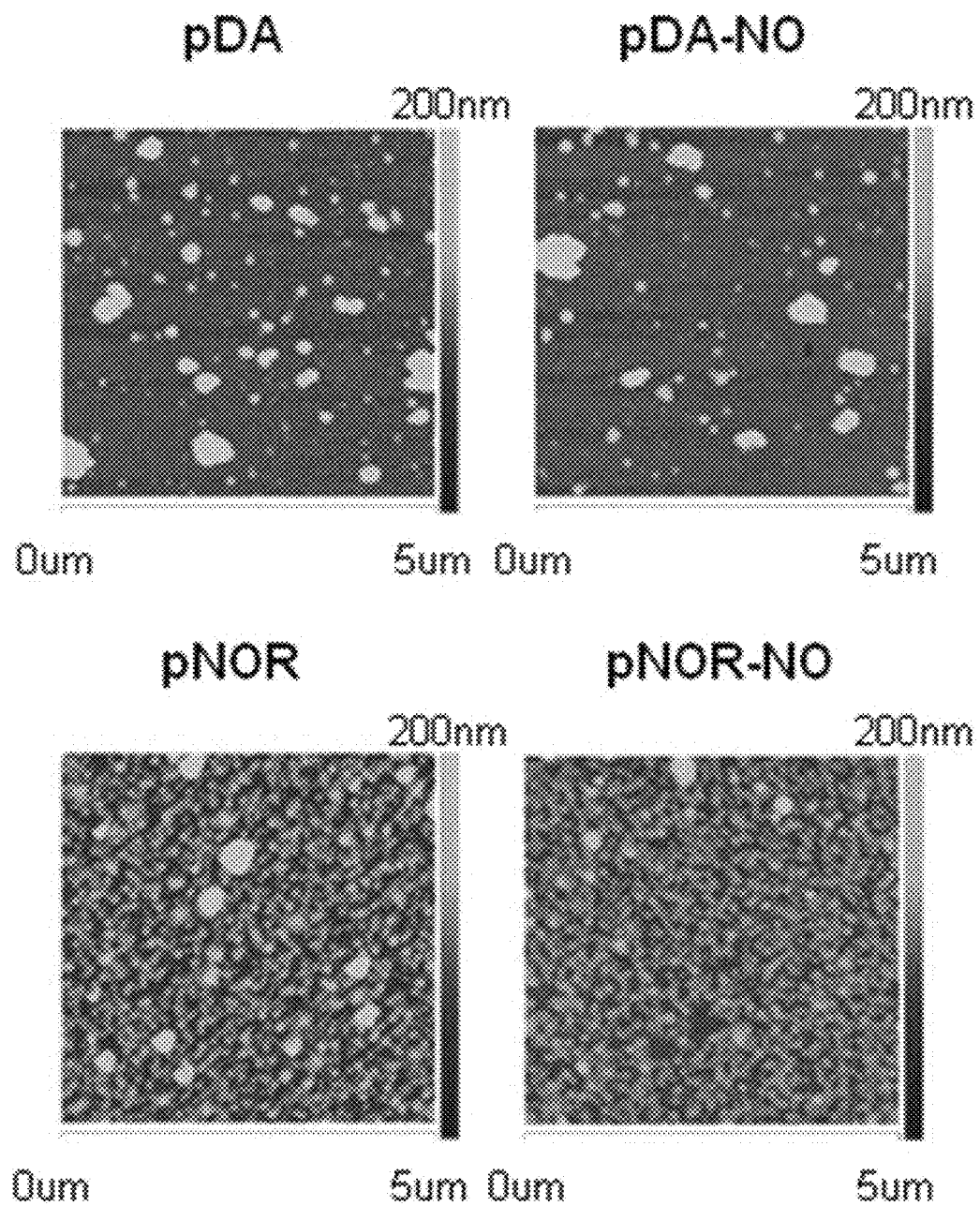
FIG. 3 is an image obtained by analyzing surfaces of the coating films prepared according to one exemplary embodiment of the present invention using an atomic force microscope (AFM)

From the results obtained by observing nanostructures of the 4 kinds of coating films, it was revealed that the dopamine polymer coating film exhibited lack of uniformity in coatability, compared with the norepinephrine polymer coating films, as shown in FIG. 3. Also, it was revealed that the dopamine polymer coating films and the norepinephrine polymer coating films did not exhibit a significant apparent change in surface shape even after attachment of the diazeniumdiolate functional group, which indicated that there was no effect of strong alkali and pressure on the structures of the catecholamine polymer coating films having nitrogen monoxide formed therein. Referring to the results of the following Table 1 obtained by quantifying the AFM analysis results, however, it was confirmed that a decrease in surface roughness was observed after attachment of the diazeniumdiolate functional group.

From the results, it could be seen that the coating film according to the present invention did not exhibit disadvantages such as a change in shape of the coating film even under the strong alkali conditions or in the presence of nitrogen monoxide, but a decrease in roughness was observed. As a result, it was reasoned that change in structure of the thin film was caused.

TABLE 1

| Materials | Roughness (nm) | Surface area ($\mu m^2/25.0\ \mu m^2$) |
| --- | --- | --- |
| Bare surface | 0.1 ± 11 | 25 |
| pDA | 66.0 ± 28.8 | 28.5 ± 0.3 |
| pNOR | 28.6 ± 1.0 | 30.5 ± 1.5 |
| pDA-NO | 45.3 ± 5.7 | 28.0 ± 0.4 |
| pNOR-NO | 12.4 ± 2.5 | 27.0 ± 2.9 |

<1-2> Analysis of Characteristics of Catecholamine Polymer Coating Film Containing Diazeniumdiolate Functional Group Using Surface Contact Angle Meter Each of a dopamine polymer coating film (pDA), a dopamine polymer coating film (pDA-NO) containing a diazeniumdiolate functional group, a norepinephrine polymer coating film (pNOR), and a norepinephrine polymer coating film (pNOR-NO) containing a diazeniumdiolate functional group was formed on stainless steel using the same method as described in Preparative Example 1. Then, a structure of each coating film was observed using a surface contact angle meter (Phoenix 300 Goniometer, Surface Electro Optics Co., Ltd. Korea).

TABLE 2

| Materials | Contact angle (°) |
|---|---|
| Bare surface | 73.0 ± 3.96 |
| pDA | 55.2 ± 1.61 |
| pNOR | 51.4 ± 2.93 |
| pDA-NO | <10 |
| pNOR-NO | <10 |

Figure 4:
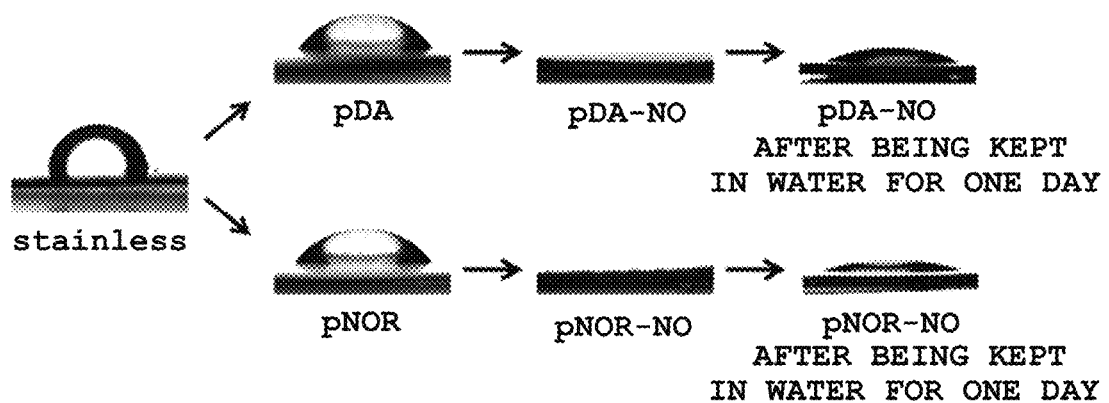
FIG. 4 is an image obtained by analyzing the surfaces of the coating films prepared according to one exemplary embodiment of the present invention using a surface contact angle meter.

Water was dropped on the coating films, and shapes of droplets were observed using a surface contact angle meter. The results were shown in FIG. 4 and listed in Table 2. In Table 2, it was understood that a hydrophobic property increased with an increase in contact angle. Accordingly, it could be seen that the dopamine polymer coating films and the norepinephrine polymer coating films had increased hydrophilic properties, compared with the uncoated stainless steel, and thus the droplets on the coating films were close to an oval shape. The coating film having a diazeniumdiolate functional group attached thereto had more hydrophilic properties due to zwitterionic characteristics of the diazeniumdiolate functional group. As a result, it could be seen that the droplets spread without maintaining the droplet shape. However, after the release of nitrogen monoxide was somewhat induced by immersing the coating film in deionized water (D.W.) for a day to cleave a diazeniumdiolate functional group, the shapes of the droplets were observed again. As a result, it was confirmed that the shapes of the droplets returned to oval shapes, which indicated that the hydrophilic properties of the catecholamine polymer coating films containing a diazeniumdiolate functional group were due to the diazeniumdiolate functional group.

<1-3> Measurement of Thickness and Refractive Index of Catecholamine Polymer Coating Film Containing Diazeniumdiolate Functional Group Using Ellipsometry Each of a dopamine polymer coating film (pDA), a dopamine polymer coating film (pDA-NO) containing a diazeniumdiolate functional group, a norepinephrine polymer coating film (pNOR), and a norepinephrine polymer coating film (pNOR-NO) containing a diazeniumdiolate functional group was formed on a silicon wafer using the same method as described in Preparative Example 1. Then, thicknesses and refractive indexes of the coating films were measured using ellipsometry (spectroscopic ellipsometer, M2000D, JA Woollam Inc., USA).

Figure 5:
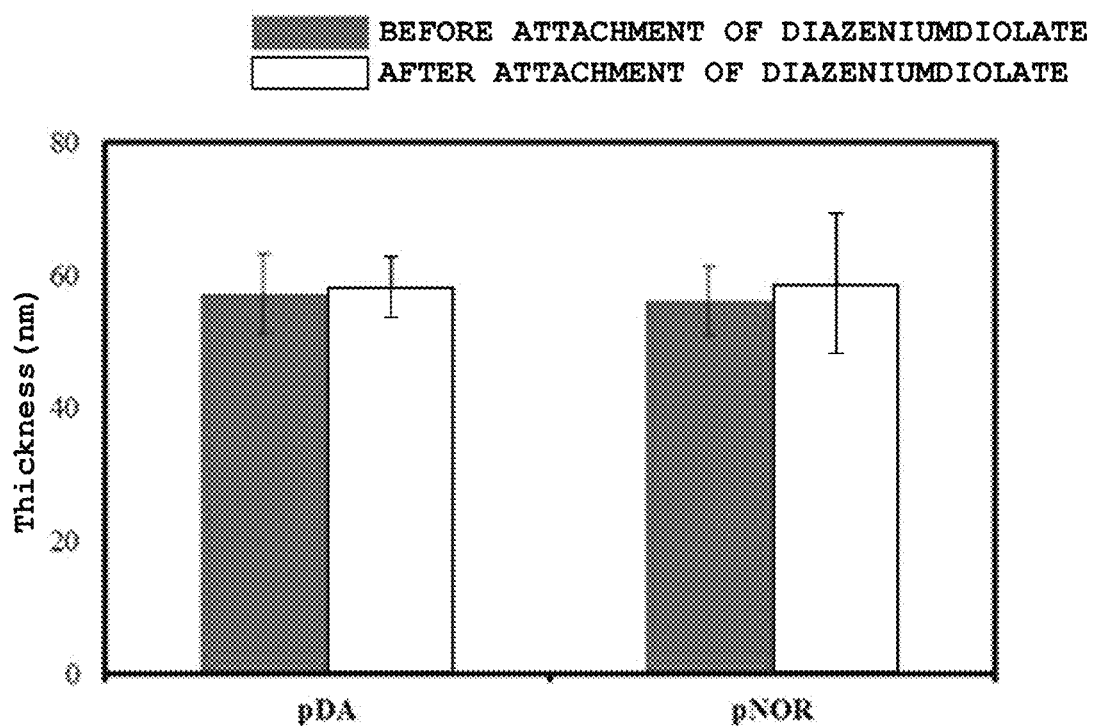
FIG. 5 shows the results obtained by analyzing thicknesses of the coating films prepared according to one exemplary embodiment of the present invention using ellipsometry.

From the results obtained by measuring the thicknesses of the coating films before and after attachment of the diazeniumdiolate functional group, it could be seen that the entire thicknesses of the thin films were maintained under the conditions in which nitrogen monoxide was introduced at a strong alkali and pressure to attach a diazeniumdiolate functional group, as shown in FIG. 5.

Figure 6:
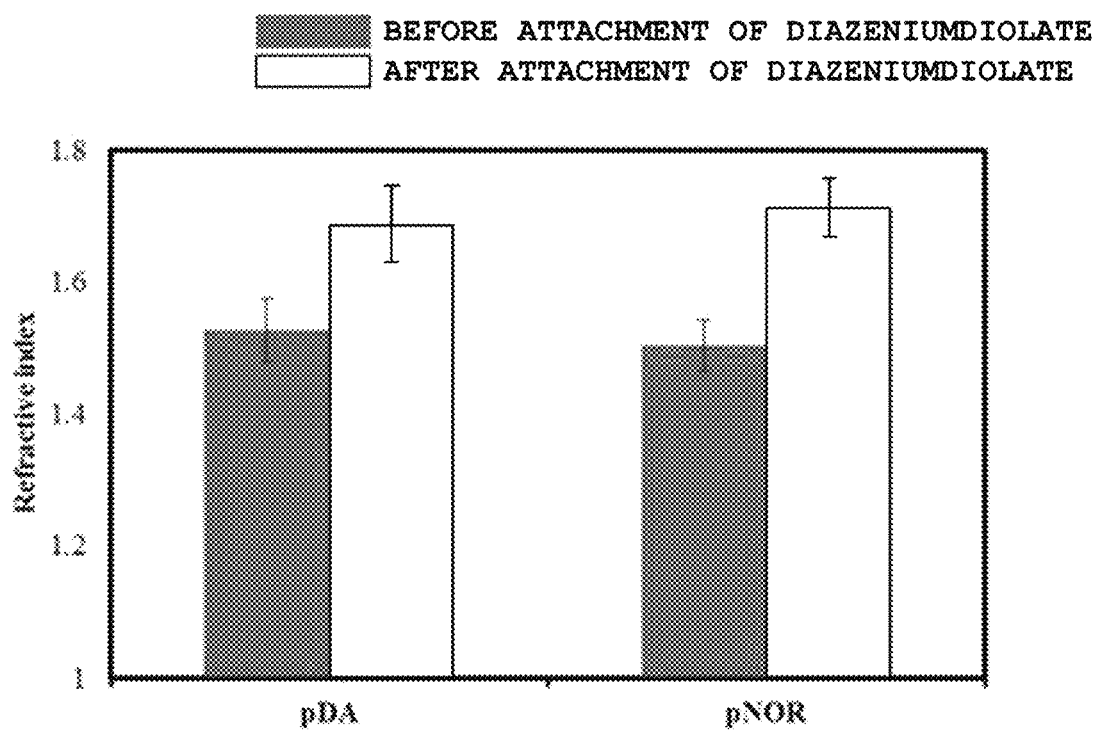
FIG. 6 shows the results obtained by analyzing refractive indexes of the coating films prepared according to one exemplary embodiment of the present invention using ellipsometry.

From the results obtained by measuring the refractive indexes of the coating films before and after attachment of the diazeniumdiolate functional group, it could be also seen that the refractive index of light increased due to the presence of the diazeniumdiolate functional group, as shown in FIG. 6.

From the results, it could be seen that the physical properties of the thin films changed without causing damage to the thin films even when the diazeniumdiolate functional group was attached to a surface of the catecholamine such as dopamine or norepinephrine.

<1-4> Confirmation of Diazeniumdiolate Functional Group Using Fourier Transform Infrared Spectroscopy Each of a dopamine polymer coating film (pDA), a dopamine polymer coating film (pDA-NO) containing a diazeniumdiolate functional group, a norepinephrine polymer coating film (pNOR), and a norepinephrine polymer coating film (pNOR-NO) containing a diazeniumdiolate functional group was formed on stainless steel using the same method as described in Preparative Example 1. Then, the presence of the diazeniumdiolate functional group was confirmed using a reflection mode of Fourier transform infrared spectroscopy (Thermo Nicolet Nexus FT-IR spectrophotometer equipped with a smart aperture grazing angle (SAGA)).

Figure 7:
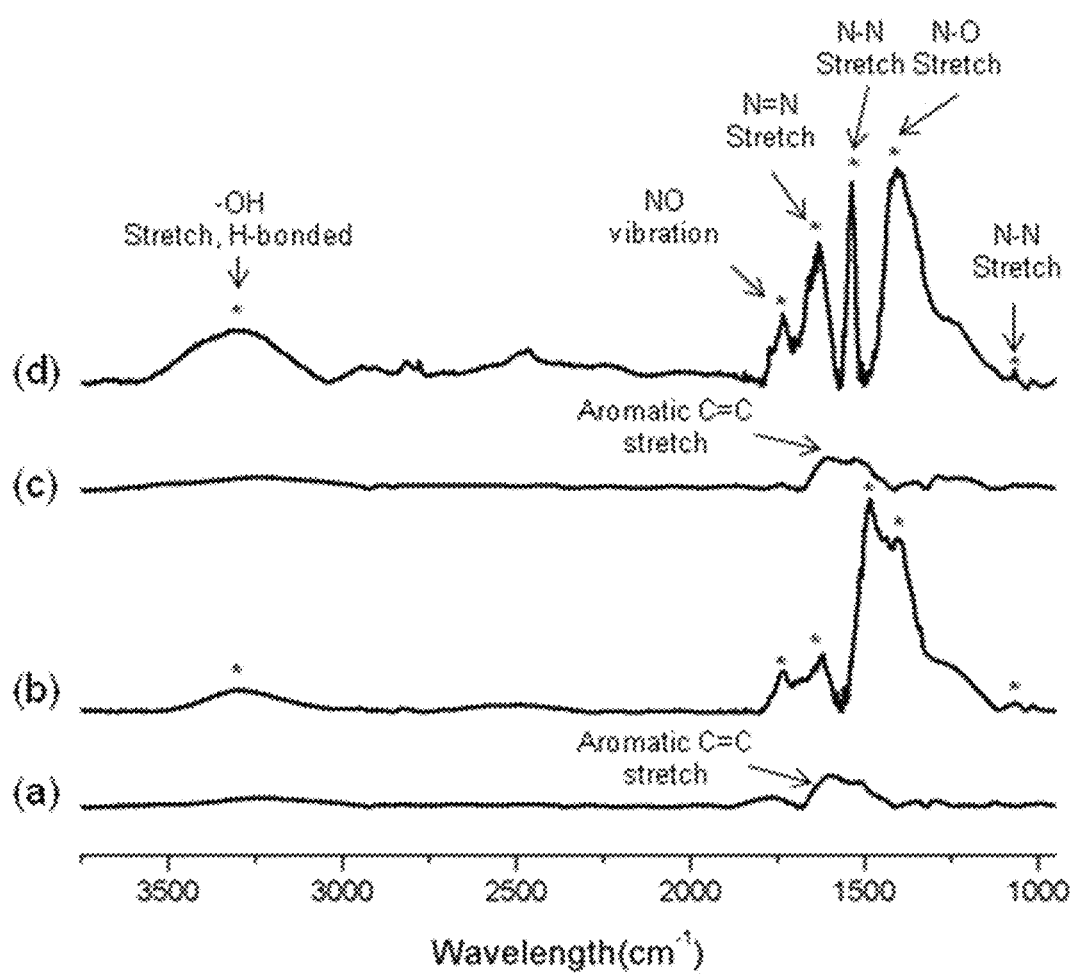
FIG. 7 shows the results obtained by analyzing functional groups of the coating films prepared according to one exemplary embodiment of the present invention using Fourier transform infrared spectroscopy (FT-IR)

From the results obtained by confirming the presence of the functional group in the thin films observed by the Fourier transform infrared spectroscopy, it was confirmed that, unlike the dopamine polymer coating film or norepinephrine polymer coating film which did not contain the diazeniumdiolate functional group, the dopamine polymer coating film or norepinephrine polymer coating film which contained the diazeniumdiolate functional group showed characteristic peaks such as N—N stretches at 1,068 $cm^{-1}$ and 1,480 to 1,540 $cm^{-1}$, an N—O stretch at 1,390 to 1,410 $cm^{-1}$, and NO vibration at 1,735 $cm^{-1}$ on the Fourier transform infrared spectroscopy, as shown in FIG. 7, which indicated that the diazeniumdiolate functional group was successfully formed on the catecholamine polymer coating films.

<1-5> Analysis of Elements of Catecholamine Polymer Coating Film Containing Diazeniumdiolate Functional Group Using X-Ray Photoelectron Spectroscopy Each of a dopamine polymer coating film (pDA), a dopamine polymer coating film (pDA-NO) containing a diazeniumdiolate functional group, a norepinephrine polymer coating film (pNOR), and a norepinephrine polymer coating film (pNOR-NO) containing a diazeniumdiolate functional group was formed on a silicon wafer using the same method as described in Preparative Example 1. Then, changes in elements in the coating films were measured using X-ray photoelectron spectroscopy (an ESCALAB 200iXL spectrometer, VG Scientific Inc, USA).

Figure 8:
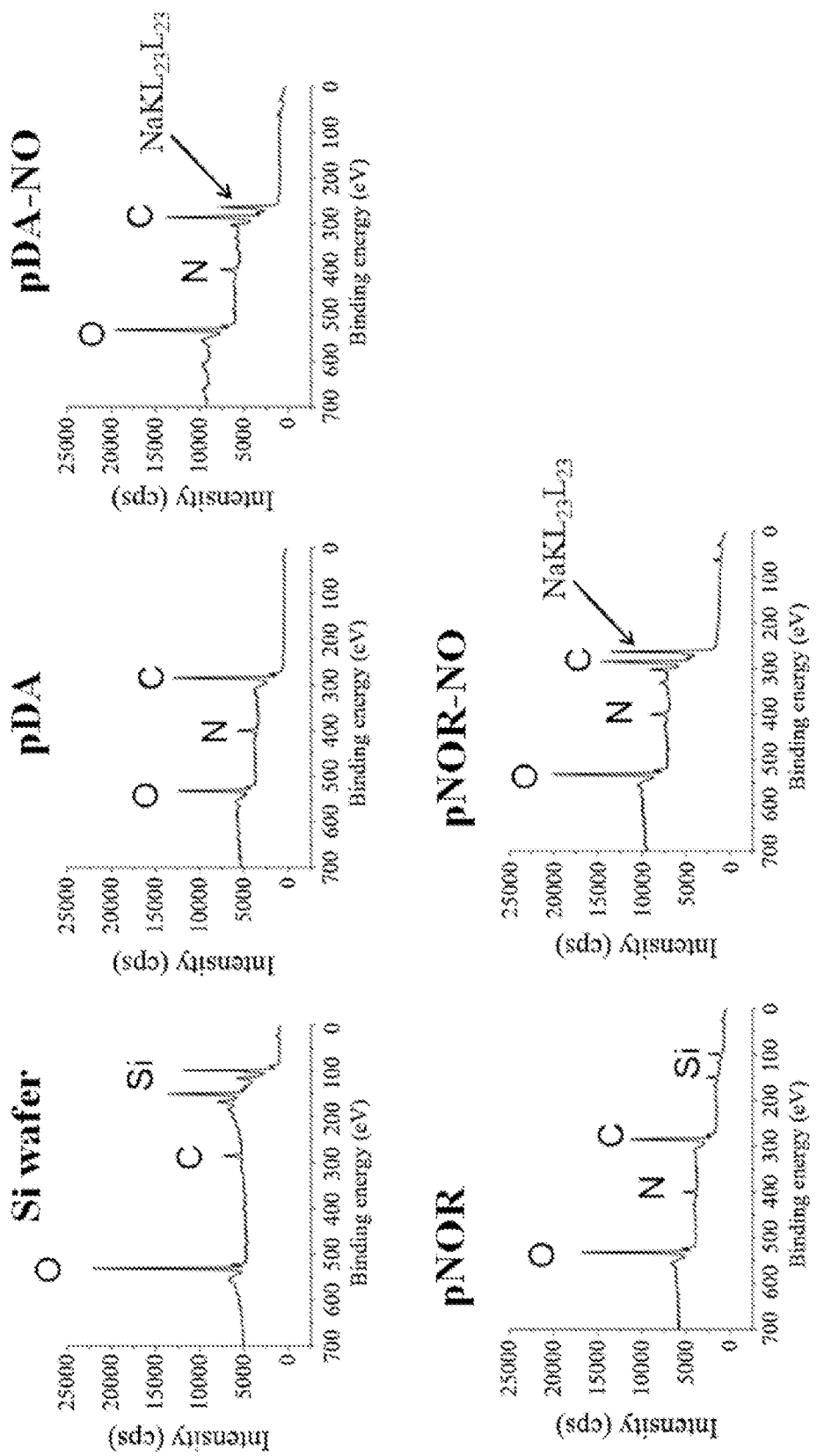
FIG. 8 shows the results obtained by analyzing elements of the coating films prepared according to one exemplary embodiment of the present invention using X-ray photoelectron spectroscopy (XPS)

From the results obtained by detecting the kinds of elements using X-ray photoelectron spectroscopy, it could be seen that no amine was present in a conventional silicon wafer for analysis, as shown in FIG. 8. However, when the silicon wafer for analysis was coated with a catecholamine polymer such as dopamine or norepinephrine, the amine was detected on a surface of the silicon wafer for analysis at a binding energy of 399.5 eV. Also, it was revealed that, when the silicon wafer for analysis was coated with a catecholamine polymer, a peak of a Si element having a binding energy of 98.5 eV decreased or disappeared, which indicated that a surface of the silicon wafer for analysis was completely coated with the catecholamine such as dopamine or norepinephrine.

Figure 9:
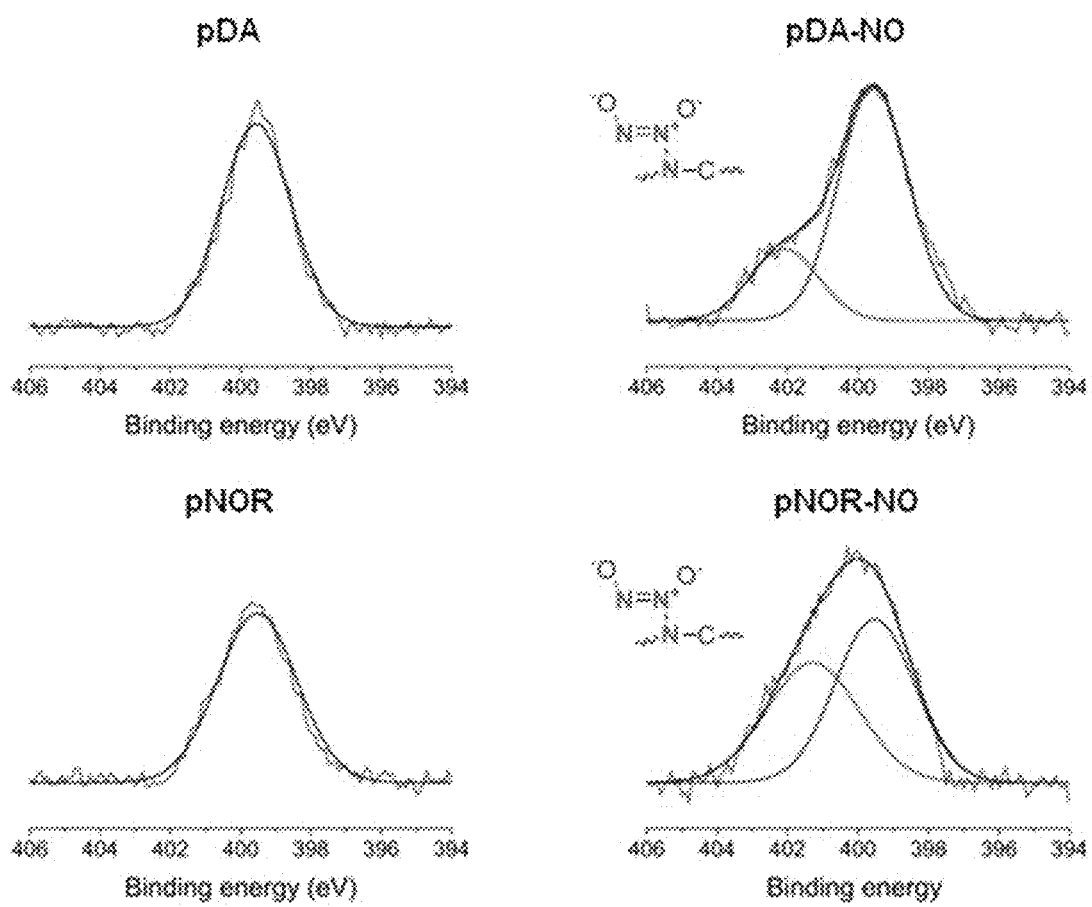
FIG. 9 shows the results obtained by analyzing amine elements of the coating films prepared according to one exemplary embodiment of the present invention using high-power X-ray photoelectron spectroscopy (XPS)

From the results obtained by fully detecting the amine using X-ray photoelectron spectroscopy, it could be seen that, when the silicon wafer for analysis was coated with dopamine and norepinephrine, the position and size of the preexisting amine peak appearing at a binding energy of 399.5 eV were not changed after attachment of the diazeniumdiolate functional group, but a new amine peak appeared at a binding energy of 402.1 eV when the silicon wafer for analysis was coated with the dopamine and appeared at a binding energy of 401.3 eV when the silicon wafer for analysis was coated with the norepinephrine, as shown in FIG. 9, which indicated that a new amine was formed on the coating films due to formation of the diazeniumdiolate having high electronegativity.

Figure 10:
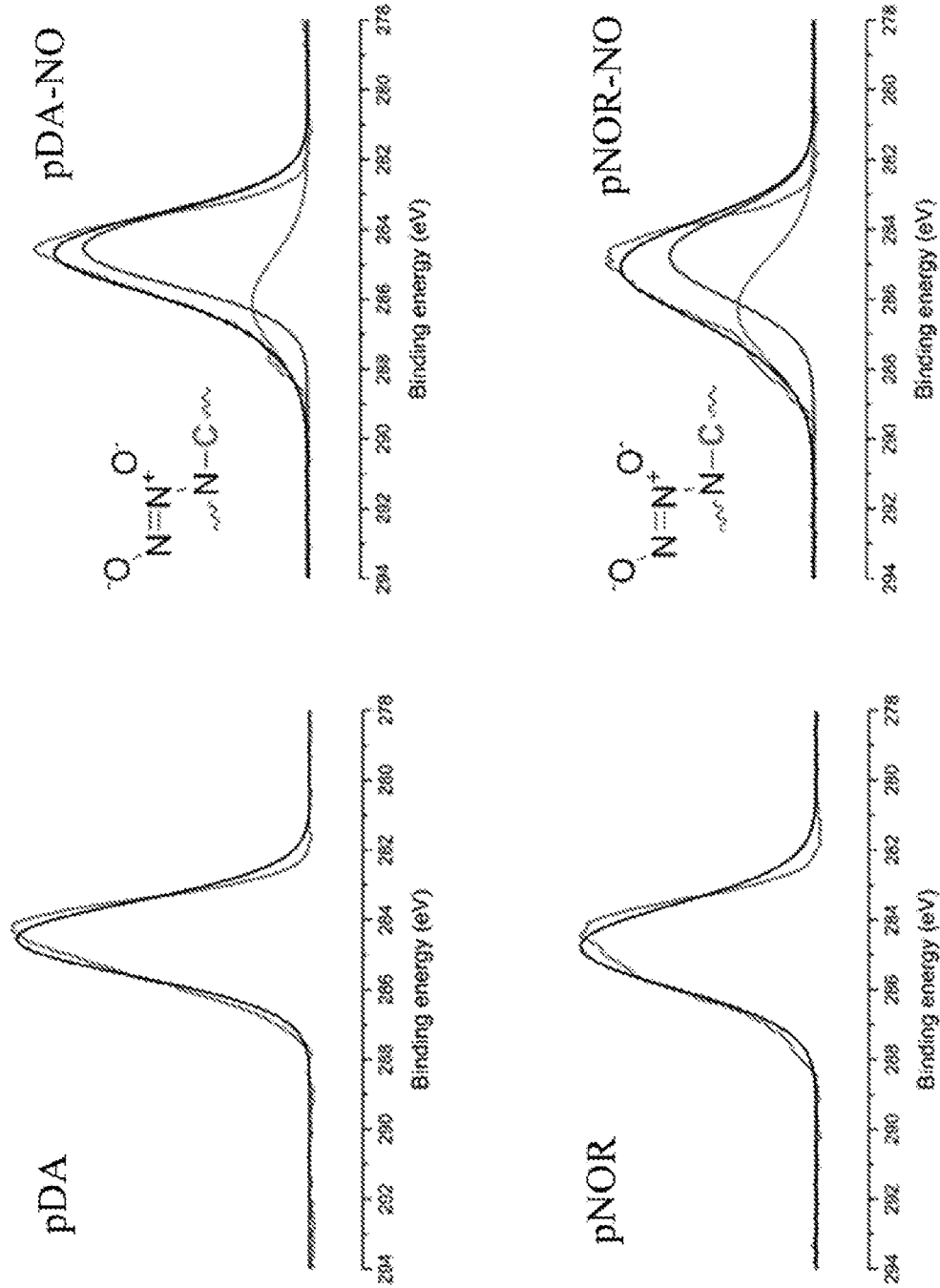
FIG. 10 shows the results obtained by analyzing carbon elements of the coating films prepared according to one exemplary embodiment of the present invention using high-power X-ray photoelectron spectroscopy (XPS)

From the results obtained by fully detecting carbon (C) using X-ray photoelectron spectroscopy, it could be seen that there was no change in the entire size of the carbon peak derived from the dopamine and the norepinephrine to which the diazeniumdiolate functional group was attached, as shown in FIG. 10, which indicated that the entire size of the carbon peak was not changed since an amount of the amine increased but there was no change in amount of carbon (C) when the diazeniumdiolate functional group was attached to the coating film. However, it could be seen that some of the peaks present only at a binding energy of 284.5 eV before attachment of the diazeniumdiolate functional group were up-shifted to 286.1 eV and 286.3 eV in the case of the dopamine and the norepinephrine, respectively. These results were derived from the fact that an increase in binding energy of carbon (C) around the amine to which the diazeniumdiolate functional group was attached was caused due to high electronegativity.

From the results, it could be seen that the diazeniumdiolate functional group was attached to the dopamine or norepinephrine polymer coating films.

TABLE 3

| Materials | N/C ratio |
|---|---|
| Bare surface | 0 |
| pDA | 0.10 |
| pNOR | 0.09 |
| pDA-NO | 0.13 |
| pNOR-NO | 0.16 |

Also, the results obtained by quantifying a ratio of the amine and carbon (C) shown in FIGS. 9 and 10 are listed in Table 3. A high N/C ratio means that there was a relatively large amount of amine. Therefore, it was confirmed that the diazeniumdiolate functional group was successfully formed on the dopamine or norepinephrine polymer coating films since the N/C ratio was higher in the coating films containing the diazeniumdiolate functional group than the coating films which did not contain the diazeniumdiolate functional group.

In addition, it could be seen that the diazeniumdiolate functional group was included at a higher amount in the norepinephrine polymer coating films containing the diazeniumdiolate functional group, compared with the dopamine polymer coating films containing the diazeniumdiolate functional group.

<1-6> Analysis of Release Characteristics of Nitrogen Monoxide from Catecholamine Polymer Coating Film Containing Diazeniumdiolate Functional Group Using Chemiluminescence Nitric Oxide Analyzer (NOAz)

Each of a dopamine polymer coating film (pDA), a dopamine polymer coating film (pDA-NO) containing a diazeniumdiolate functional group, a norepinephrine polymer coating film (pNOR), and a norepinephrine polymer coating film (pNOR-NO) containing a diazeniumdiolate functional group was formed on stainless steel using the same method as described in Preparative Example 1. Then, the release behavior of nitrogen monoxide was examined using a chemiluminescence nitric oxide analyzer (NOAz) (Sievers NOA 280i chemiluminescence NO analyzer, GE analytical instruments, USA). In this case, a principle of the chemiluminescence nitric oxide analyzer (NOAz) used to detect nitrogen monoxide was as shown in the following Formula 6. That is, nitrogen monoxide was reacted with ozone to form excited nitrogen dioxide, which was then broken down to emit chemiluminescence. In this case, since the chemiluminescence was quantitatively emitted, the released nitrogen monoxide could be quantitatively detected by quantitatively detecting the chemiluminescence.

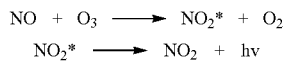

Formula 6

Figure 11:
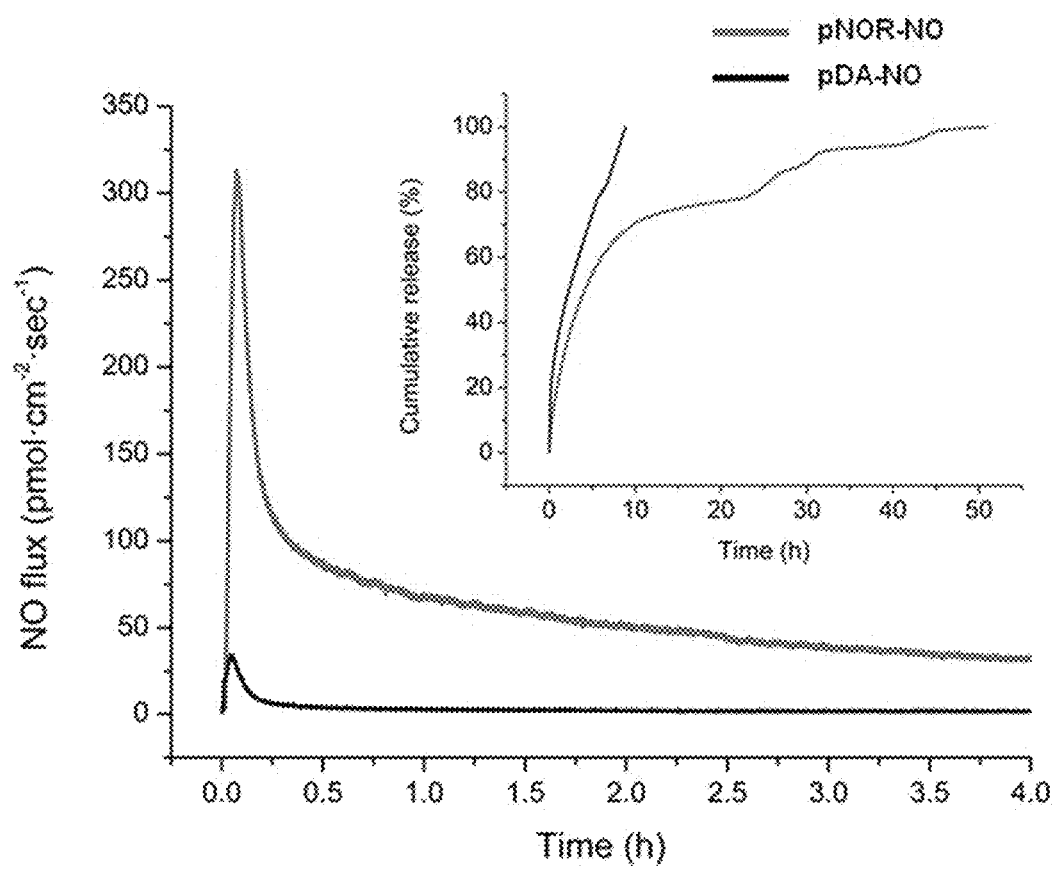
FIG. 11 is a graph showing the release characteristics of nitrogen monoxide released from the coating films prepared according to one exemplary embodiment of the present invention (pNOR-NO: a norepinephrine-added coating film, and pDA-NO: a dopamine-added coating film)

The release characteristics of nitrogen monoxide were examined by detecting the nitrogen monoxide, which was released from the dopamine or norepinephrine polymer coating films containing the diazeniumdiolate functional group under the in vivo conditions (pH 7.0, and 37° C.), in a real-time manner using the chemiluminescence nitric oxide analyzer (NOAz). As a result, it could be seen that the release characteristics of nitrogen monoxide varied according to the kind of the catecholamine used, as shown in FIG. 11. In this case, FIG. 11 is a graph plotted by converting an entire amount of the nitrogen monoxide released in a real-time manner into a percentage (%). The results are quantitatively summarized and listed in the following Table 4.

TABLE 4

| Materials | $[NO]_t$ (nmol · $cm^{-2}$)[b] | $t_d$ (h)[c] | $[NO]_m$ (pmol · $cm^{-2}$ · $sec^{-1}$)[d] | $t_m$ (min)[e] | $t_{1/2}$ (h)[f] |
|---|---|---|---|---|---|
| pDA-NO | 69.5 | 8.93 | 34.8 | 2.95 | 2.30 |
| pNOR-NO | 1789 | 50.9 | 313.0 | 4.40 | 4.16 |

In Table 4, $[NO]_t$ represents a total amount of nitrogen monoxide (nanomole units: nmol·$cm^{-2}$) stored per square centimeter ($cm^2$), $[NO]_m$ represents the maximum amount of nitrogen monoxide (picomole units: pmol·$cm^{-2}$·$sec^{-1}$) released per square centimeter each second, $t_d$ represents a time (units: day) required to release all the nitrogen monoxide, $t_m$ represents a time (units: min) required to reach $[NO]_m$ after the first release of nitrogen monoxide, and $t_{1/2}$ represents a time (units: hours) required to release 50% of the stored nitrogen monoxide. It could be seen from $[NO]_t$ and $[NO]_m$ that the norepinephrine polymer coating films stored and instantly released a larger amount of nitrogen monoxide than the dopamine polymer coating films. Also, it could be seen from $t_d$ and $t_{1/2}$ that the norepinephrine polymer coating films released the nitrogen monoxide more slowly than the dopamine polymer coating films. This difference was caused by a structural difference of an alkyl group present in a para-position of a catechol group of the norepinephrine. It could be seen that, since the norepinephrine had an additional hydroxyl group at an alkyl amine, compared with the dopamine, the norepinephrine could form a hydrogen bond with the diazeniumdiolate functional group, which is desirable for storage and slow release of the nitrogen monoxide.

Therefore, the coating films prepared using the method according to the present invention are expected to be used to heal a disease, for example, used to heal a wound or prevent vascular restenosis, since the coating films slowly released the nitrogen monoxide. Also, it was revealed that the dopamine polymer coating films containing a diazeniumdiolate functional group released the nitrogen monoxide very quickly. Therefore, the dopamine polymer coating films are expected to be used to treat a bacteria- or virus-mediated disease using such quick release of nitrogen monoxide.

From the results, it was proven that the release of nitrogen monoxide was able to be controlled using the catecholamine containing various functional groups.

<1-7> Evaluation of Antibacterial Activity of Catecholamine Polymer Coating Film Containing Diazeniumdiolate Functional Group The present inventors examined an antibacterial effect of the coating film for enabling controlled release of nitrogen monoxide according to the present invention as one field to which the coating film was applicable. In general, it was reported that nitrogen monoxide exhibited an antibacterial effect by inhibiting the functions and synthesis of proteins or DNA in bacteria. In this case, the antibacterial effect included all kinds of abilities to prevent bacteria from adsorbing to a surface of a material and kill bacteria. To examine the antibacterial effect, a dopamine polymer coating film (pDA), a dopamine polymer coating film (pDA-NO) containing a diazeniumdiolate functional group, a norepinephrine polymer coating film (pNOR), and a norepinephrine polymer coating film (pNOR-NO) containing a diazeniumdiolate functional group were formed on stainless steel using the same method as described in Preparative Example 1. Then, an antibacterial effect was determined using S. epidermidis, which is a bacterial strain known to cause actual infections during clinical surgery of a body-implantable material. That is, 1 mL of a bacterial solution of S. epidermidis grown in 3 mL of a tryptic soy broth (TSB) at 37° C. for 14 hours while shaking was added to 30 mL of TSB, and incubated for 2 hours at 37° C. while shaking. 50 μL of the bacterial solution and 3 mL of Dellbuco's phosphate buffered saline (DPBS) were added to each well of a 12-well plate, and each of the coating film samples was added, and kept at 37° C. for an hour to allow bacteria to adsorb onto a surface of each sample. After an hour, each of the samples was washed twice with water to remove unadsorbed bacteria. Then, adsorption of the bacteria was observed using an inverted optical microscope (Nikon eclipse L150, Nikon Instruments Inc., Japan).

Figure 12:
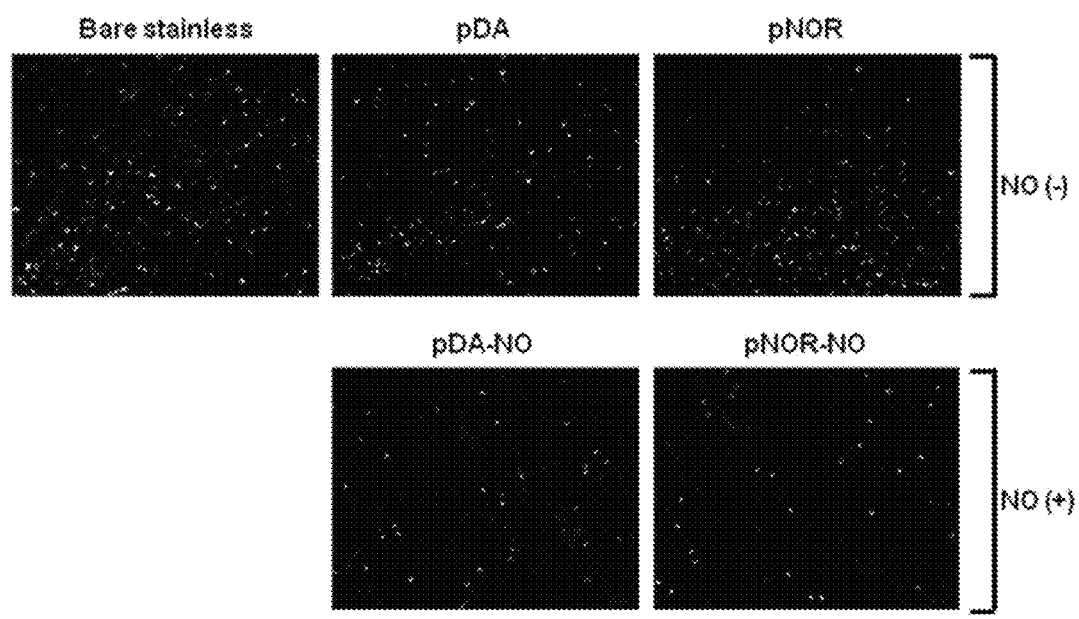
FIG. 12 is an image illustrating the effects of the coating films prepared according to one exemplary embodiment of the present invention on prevention of bacterial adsorption.

From the results obtained by examining the adsorption prevention activity in an aqueous solution in which bacteria were grown, it could be seen that a significantly lower amount of bacteria was adsorbed onto the dopamine or norepinephrine polymer coating films, which contained the diazeniumdiolate functional group capable of releasing nitrogen monoxide, compared with the dopamine or norepinephrine polymer coating films which did not contain the diazeniumdiolate functional group, as shown in FIG. 12.

Figure 13:
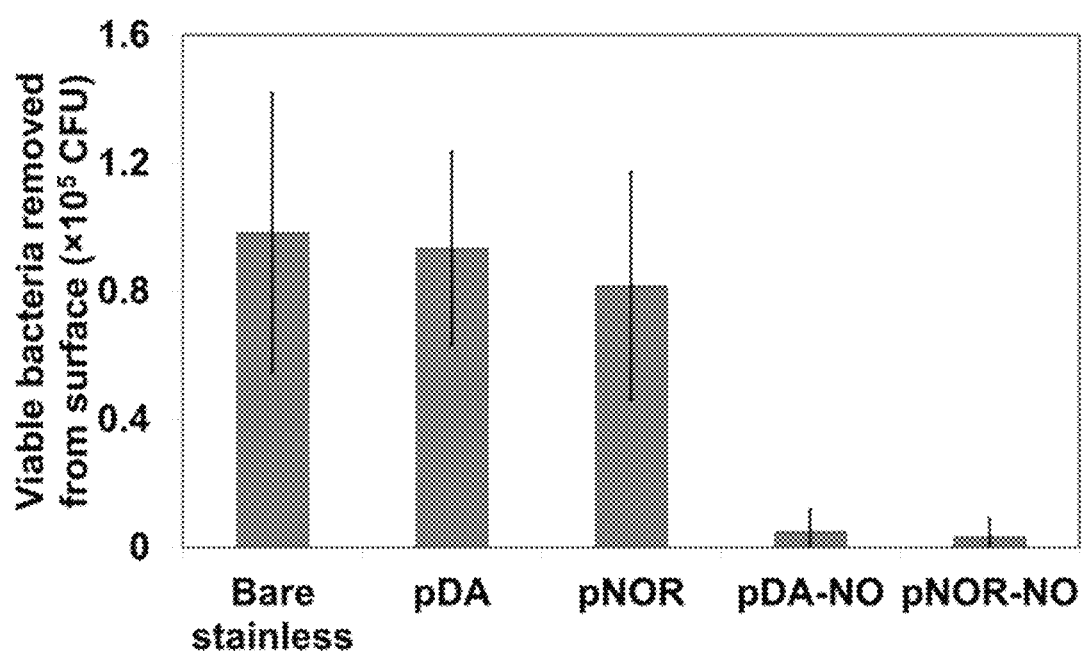
FIG. 13 is a graph illustrating the effects of the coating films prepared according to one exemplary embodiment of the present invention on inhibition of bacterial growth.

From the results obtained by quantitatively measuring an amount of living bacteria attached to surfaces of the coating films, it could be also seen that approximately 97% of the bacteria died in the dopamine or norepinephrine polymer coating films containing the diazeniumdiolate functional group capable of releasing nitrogen monoxide, which was higher than that of the dopamine or norepinephrine polymer coating films which did not contain the diazeniumdiolate functional group, as shown in FIG. 13.

From the results, it could be seen that the coating films prepared by the method according to the present invention had an antibacterial effect.

<1-8> Evaluation of Cytotoxicity of Catecholamine Polymer Coating Film Containing Diazeniumdiolate Functional Group The catecholamine used in the present invention was a material biosynthesized at a higher level than PLGA which has been approved by the FDA, but there was no report on toxicity of the catecholamine containing a diazeniumdiolate functional group. From this fact, cytotoxicity was evaluated to search for actual applicability of the coating films prepared in the present invention to a body-implantable material and/or a medical appliance.

Each of a dopamine polymer coating film (pDA), a dopamine polymer coating film (pDA-NO) containing a diazeniumdiolate functional group, a norepinephrine polymer coating film (pNOR), and a norepinephrine polymer coating film (pNOR-NO) containing a diazeniumdiolate functional group was formed on stainless steel using the same method as described in Preparative Example 1. Then, the cytotoxicity was evaluated in a mammalian fibroblast (i.e., an NIH/3T3 cell line).

Figure 14:
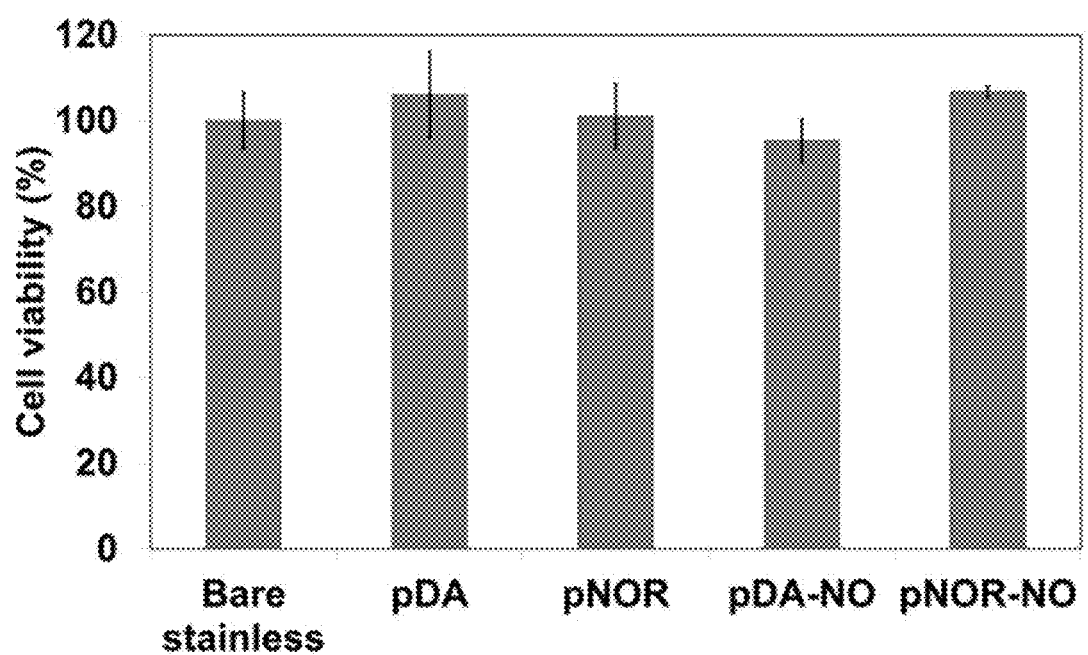
FIG. 14 shows the results obtained by testing whether the coating films prepared according to one exemplary embodiment of the present invention exhibit toxicity in cells.

As a result, it could be seen that the coating film having a diazeniumdiolate functional group attached thereto according to the present invention did not exhibit any toxicity in mammalian cells, as shown in FIG. 14.

From the results, it could be seen that the coating film for enabling controlled release of nitrogen monoxide prepared by the method according to the present invention can be safely used since the coating film does not exhibit cytotoxicity, and thus can be widely used for various body-implantable materials and medical appliances.

According to the present invention, a technique for preparing a coating film having a small thickness capable of control-releasing nitrogen monoxide from the surfaces of the various materials can be provided, and the preparation technique is simplified, inexpensive and economical.

Also, the coating film prepared by the method according to the present invention has advantages in that nitrogen monoxide can be stably supplied under an in vivo environment, and can be suitably used in a living body without causing cytotoxicity. Therefore, when the coating film according to the present invention is prepared using a body-implantable material as the material, the body-implantable material is especially expected to be widely used for medical and health applications including treatment of ischemic disorders such as arteriosclerosis through controlled release of nitrogen monoxide, regulation of penile erections, antibacterial and antiviral effects, and wound healing.

While the invention has been shown and described with reference to certain exemplary embodiments thereof, it will be understood by those skilled in the art that various changes in form and details may be made therein without departing from the scope of the invention as defined by the appended claims.

What is claimed is:

1. A method of preparing a nitrogen-monoxide-containing coating film on a surface of a material comprising:
 (a) immersing a material whose surface is to be coated in a basic solution at pH 8.5 to pH 11, wherein said basic solution is at least one solution selected from the group consisting of a physiological saline solution, water, and tetrahydrofuran (THF);
 (b) adding a catecholamine to the basic solution used in operation (a) and keeping the material in the resulting mixture to form a catecholamine polymer coating film;
 (c) drying the material after the keeping of the material in operation (b);
 (d) introducing the material dried in operation (c) into a reactor containing another basic solution which contains one or more of sodium methoxide (NaOMe), methanol (MeOH), tetrahydrofuran (THF), or sodium hydroxide (NaOH);

(e) purging the reactor used in operation (d) with argon (Ar) gas; and (f) introducing nitrogen monoxide into the reactor used in operation (e) to synthesize a diazeniumdiolate on a surface of the catecholamine polymer coating film.

2. The method according to claim 1, wherein the keeping of the material in operation (b) is performed for 6 to 72 hours.

3. The method according to claim 1, wherein the catecholamine added in operation (b) is in the form of powder or an aqueous solution obtained by dissolving the powder.

4. The method according to claim 1, wherein the drying of the material in operation (c) is performed using argon (Ar), helium (He), or nitrogen ($N_2$) gas.

5. The method according to claim 1, wherein the basic solution used in operation (d) is present at a concentration of 0.1 to 0.5 M.

6. The method according to claim 1, wherein the purging of the reactor in operation (e) is performed one to three times at a pressure of 10 to 30 psi.

7. The method according to claim 1, wherein the introducing of the nitrogen monoxide in operation (f) is performed at a pressure of 80 to 150 psi.

8. The method according to claim 1, further comprising: sonicating the material in methanol after operation (f).

9. The method according to claim 1, wherein the catecholamine is selected from the group consisting of dopamine, dopamine quinone, alpha-methyldopamine, norepinephrine, dihydroxyphenylalanine (DOPA), alpha-methyldopa, droxidopa, and 5-hydroxydopamine.

10. The method according to claim 1, wherein the coating film has a thickness of 40 to 60 nm.

11. The method according to claim 1, wherein the material is a body-implantable material selected from the group consisting of a stent, a catheter, a subcutaneous implant, a chemical sensor, a lead, a pacemaker, a vascular graft, a wound dressing, a penile implant, an implantable pulse generator, an implantable cardiac defibrillator, and a nerve stimulator.

* * * * *